United States Patent
Lee et al.

(10) Patent No.: US 12,303,530 B2
(45) Date of Patent: May 20, 2025

(54) COMBINATION THERAPY OF CYCLOSERINE AND LITHIUM FOR THE TREATMENT OF DEPRESSION

(71) Applicant: NEURORIVE INC, Seoul (KR)

(72) Inventors: Sukchan Lee, Yongin-si (KR); Yong Ha Chi, Seogwipo-si (KR); Dong Cheol Jang, Wonju-si (KR); Gibeom Kwon, Suwon-si (KR)

(73) Assignee: NEURORIVE INC, Seoul (KR)

( * ) Notice: Subject to any disclaimer, the term of this patent is extended or adjusted under 35 U.S.C. 154(b) by 477 days.

(21) Appl. No.: 17/771,648

(22) PCT Filed: Nov. 27, 2020

(86) PCT No.: PCT/KR2020/017101
§ 371 (c)(1),
(2) Date: Apr. 25, 2022

(87) PCT Pub. No.: WO2021/107690
PCT Pub. Date: Jun. 3, 2021

(65) Prior Publication Data
US 2022/0387481 A1    Dec. 8, 2022

(30) Foreign Application Priority Data

Nov. 27, 2019    (KR) .................. 10-2019-0154218

(51) Int. Cl.
*A61K 31/42* (2006.01)
*A61K 33/00* (2006.01)
*A61P 25/24* (2006.01)

(52) U.S. Cl.
CPC .............. *A61K 33/00* (2013.01); *A61K 31/42* (2013.01); *A61P 25/24* (2018.01)

(58) Field of Classification Search
CPC ........ A61K 33/00; A61K 31/42; A61K 33/14; A61P 25/24; A61P 25/28; A23L 33/10;
(Continued)

(56) References Cited

U.S. PATENT DOCUMENTS

2005/0261278 A1* 11/2005 Weiner .................... A61P 25/14
424/722
2009/0155389 A1* 6/2009 Weiner .................... A61P 25/24
424/715

(Continued)

FOREIGN PATENT DOCUMENTS

| EP | 2 670 409 B1 | 4/2018 |
| JP | 3-148221 A | 6/1991 |

(Continued)

OTHER PUBLICATIONS

Heninger et al. (Arch Gen Psychiatry 1983;40:1335-1342) (Year: 1983).*

(Continued)

*Primary Examiner* — Ernst V Arnold
(74) *Attorney, Agent, or Firm* — Sughrue Mion, PLLC

(57) ABSTRACT

The present invention relates to a combination therapy of cycloserine and lithium for the prevention or treatment of depression. The combined administration of cycloserine and lithium according to the present invention has a remarkably excellent effect of preventing or treating depression compared to each single administration, thereby being effectively utilized as a combination therapy for antidepressants.

6 Claims, 1 Drawing Sheet

(58) Field of Classification Search
CPC ............... A23L 33/16; A23V 2002/00; A23V 2200/322; A23V 2250/1604
See application file for complete search history.

(56) References Cited

U.S. PATENT DOCUMENTS

| | | |
|---|---|---|
| 2010/0216805 A1 | 8/2010 | Barlow et al. |
| 2013/0005783 A1 | 1/2013 | Hornemann |
| 2014/0018349 A1* | 1/2014 | Heresco-Levy ..... A61K 31/554 514/380 |

FOREIGN PATENT DOCUMENTS

| | | | |
|---|---|---|---|
| KR | 10-2009-0029200 A | 3/2009 | |
| WO | WO-2008118785 A2 * | 10/2008 | ........... A61K 31/135 |
| WO | WO-2016057533 A1 * | 4/2016 | ............. A61K 31/28 |
| WO | 2017/215992 A1 | 12/2017 | |

OTHER PUBLICATIONS

Jope, RS (Frontiers in Molecular Neuroscience 2011;4(16): 1-11) (Year: 2011).*
Duda et al. (Cells 2020;9(727): 26 pages) (Year: 2020).*
Beurel et al. (Mol Psychiatry 2011;16(11):1068-1070) (Year: 2011).*
Munoz et al. (Am Psychol 2012;67(4):285-295) (Year: 2012).*
Russian Office Action dated Jan. 31, 2023 in Russian Application No. 2022117249.
Office Action issued May 23, 2023 in Japanese Application No. 2022-524090.
Sara Costi et al., "Lithium continuation therapy following ketamine in patients with treatment resistant unipolar depression: a randomized controlled trial", Neuropsychopharmacology, 2019, vol. 44, pp. 1812-1819 (8 pages total).
Carlos A. Zarate, Jr. et al., "An Open-Label Trial of the Glutamate-Modulating Agent Riluzole in Combination with Lithium for the Treatment of Bipolar Depression", Biol Psychiatry, 2005, vol. 57, pp. 430-432 (3 pages total).
E.Rouaud et al., "D-Cycloserine facilitates synaptic plasticity but impairs glutamatergic neurotransmission in rat hippocampal slices", British Journal of Pharmacology, 2003, pp. 1051-1056, vol. 140.
Fabrice Jollant, MD, PHD, "Add-on lithium for the treatment of unipolar depression: Too often forgotten?", Journal of Psychiatry & Neuroscience, 2015, pp. E23-E24, vol. 40. No. 1.
Marc S. Lener et al., "Ketamine and Beyond: Investigations into the Potential of Glutamatergic Agents to Treat Depression", Drugs, Feb. 14, 2021, pp. 381-401, vol. 77, No. 4.
Mu-Hong Chen et al., "Maintenance of antidepressant and antisuicidal effects by D-cycloserine among patients with treatment-resistant depression who responded to low-dose ketamine infusion: a double-blind randomized placebo-control study", Neuropsychopharmacology, Aug. 17, 2019, pp. 2112-2118, vol. 44.
International Search Report for PCT/KR2020/017101 dated, Apr. 14, 2021 (PCT/ISA/210).
Written Opinion of the International Searching Authority for PCT/KR2020/017101 dated, Apr. 14, 2021 (PCT/ISA/237).
Felber, W., et al., "Lithium Clinics in Berlin and Dresden: a 50-Year Experience", Pharmacopsychiatry, vol. 51, No. 5, pp. 166-171 (6 pages).
Lewitzka, U. et al., "The suicide prevention effect of lithium: more than 20 years of evidence—a narrative review", International Journal of Bipolar Disorders 2015, vol. 3, No. 15, (16 pages).
Office Action dated Jul. 18, 2024 in New Zealand Application No. 787222.
Office Action issued Dec. 19, 2023 in Japanese Application No. 2022-524090.

\* cited by examiner

# COMBINATION THERAPY OF CYCLOSERINE AND LITHIUM FOR THE TREATMENT OF DEPRESSION

CROSS REFERENCE TO RELATED APPLICATIONS

This application is a National Stage of International Application No. PCT/KR2020/017101 filed Nov. 27, 2020, claiming priority based on Korean Patent Application No. 10-2019-0154218 filed Nov. 27, 2019, the entire disclosures of which are incorporated herein by reference.

TECHNICAL FIELD

The present invention relates to a combination therapy of cycloserine and lithium for the treatment of depression.

BACKGROUND ART

Depression is an emotional pathological phenomenon that occurs regardless of the objective situation. All of the patients' lives are covered with depressed moods, decreased interest, and anhedonia, and become obsessed with deprivation of mental exercise, a feeling of pessimism, and despair. It is a disease that leads to suicide attempts because suicide is motivated, and is manifested by a variety of physical symptoms such as decreased appetite, insomnia, constipation, loss of libido, and the like. The depression has recently emerged as a serious social problem.

Most of the current antidepressants have pharmacological actions that increase the concentration of neurotransmitters in central serotonin or noradrenaline synapses. The antidepressants that are widely used may be classified into tricyclic antidepressants (TCA), monoamine oxidase inhibitors (MAOI), selective serotonin reuptake inhibitors (SSRI), and the like, depending on mechanisms that increase the concentration of neurotransmitters. Even though these conventional antidepressants are relatively effective, in some cases, severe side effects and effects that do not meet expectations may appear. There are a number of patients who do not respond well to antidepressant drugs (Thase et al. 2001), have a high recurrence rate (Frank et al. 1991), and are not able to take the drug due to severe side effects (Gumnick and Nemeroff 2000). TCA such as imipramine, desipramine, and the like, have severe side effects such as hypotension, heart dysfunction, and the like. The most widely used SSRI such as fluoxetine, sertraline, and the like, cause nausea, gastrointestinal bleeding, sexual dysfunction, or the like.

Cycloserine (D-cycloserine; DCS) is an antibiotic substance approved under the brand name Seromycin, and is known to be a partial agonist for NMDA receptors with regard to the nervous system. Seromycin capsules, which are cycloserine used as medicament, are administered orally twice a day. The drug concentration thereof is determined in consideration of body weight, medical condition, seromycin serum level, and the like, and should not exceed 1,000 mg per day.

Lithium carbonate ($Li_2CO_3$) among lithium salts has been approved for the treatment of bipolar disorder (manic depression). It is known that lithium acts on Na+/K+ ATPase in neurons, alters the release of neurotransmitters, affects cAMP concentration, and blocks inositol metabolism, thereby depleting and inhibiting neurons.

As described above, it is known that cycloserine and the lithium salt are able to act on the central nervous system through different mechanisms, respectively, but it is not known at all that using the drugs in combination is able to effectively treat depression.

DISCLOSURE

Technical Problem

An object of the present invention is to provide a combination therapy of cycloserine and lithium for the treatment of depression.

Technical Solution

In the present invention, the inventors confirmed for the first time that when cycloserine and lithium were administered in combination, an effect of preventing or treating depression was significantly improved compared to each single administration.

In one aspect, the present invention provides a pharmaceutical composition for preventing or treating depression including: (i) cycloserine or a pharmaceutically acceptable salt thereof; and (ii) lithium or a pharmaceutically acceptable salt thereof.

In the pharmaceutical composition, the cycloserine may be D-cycloserine, and the pharmaceutically acceptable salt of lithium may be lithium carbonate, lithium chloride, lithium acetate, lithium sulfate, lithium citrate, lithium orotate, lithium gluconate, or a combination thereof.

In the pharmaceutical composition, a weight ratio of (i) the cycloserine or the pharmaceutically acceptable salt thereof; and (ii) the lithium or the pharmaceutically acceptable salt thereof may be 10:5 to 10:1, and specifically, about 2.5:1 or about 5:1. The pharmaceutical composition may include 10 to 50 mg of the cycloserine or the pharmaceutically acceptable salt thereof and 2.5 to 10 mg of the lithium or the pharmaceutically acceptable salt thereof, respectively.

In the pharmaceutical composition, the pharmaceutical composition may be administered orally.

In another aspect, the present invention provides a combination for preventing or treating depression including: (i) a first preparation including cycloserine or a pharmaceutically acceptable salt thereof; and (ii) a second preparation including lithium or a pharmaceutically acceptable salt thereof.

In the combination, the first preparation and the second preparation may be administered simultaneously or at different times. Further, the combination may be a combination preparation including the first preparation and the second preparation, and specifically may be a combination preparation administered orally.

In still another aspect, the present invention provides an adjuvant pharmaceutical composition of lithium for preventing or treating depression including cycloserine or a pharmaceutically acceptable salt thereof.

In still another aspect, the present invention provides a food composition for preventing or improving depression including: (i) cycloserine or a pharmaceutically acceptable salt thereof; and (ii) lithium or a pharmaceutically acceptable salt thereof.

Advantageous Effects

The combined administration of cycloserine and lithium according to the present invention has a remarkably excellent effect of preventing or treating depression compared to each single administration, thereby being effectively utilized as a treatment therapy or a combination preparation for antidepressants.

BEST MODE

Figure 1:
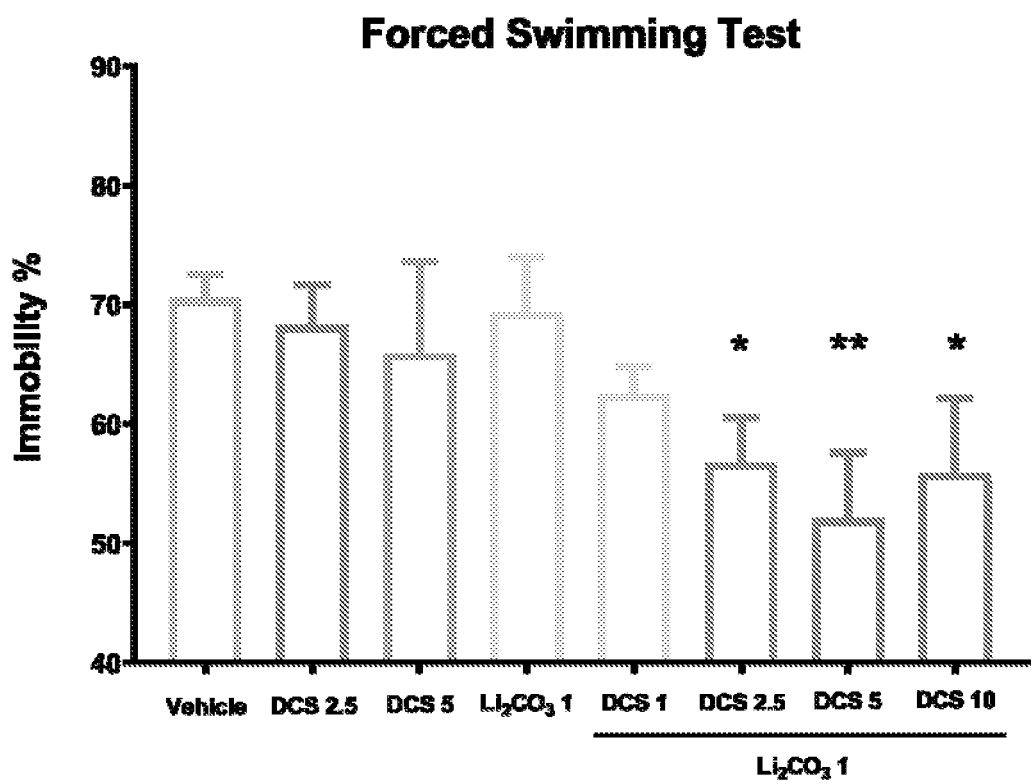
FIG. 1 shows results of a forced swimming test (FST) in mouse depending on a combination treatment of D-cycloserine and a lithium salt.

Hereinafter, the present invention will be described in detail as exemplary embodiments of the present invention with reference to the accompanying drawings. However, the following exemplary embodiments are presented as examples of the present invention, and in a case where it is determined that detailed descriptions of a technique or configuration well known to those skilled in the art may unnecessarily obscure the gist of the present invention, detailed descriptions thereof may be omitted, and thus the present invention is not limited thereto. The present invention may be variously modified and applied within the description of the claims to be described below and within the equivalent scope interpreted therefrom.

In addition, terminologies used in the present specification are terms used to appropriately express preferred embodiments of the present invention, which may vary depending on the intention of users or operators, or customs in the field to which the present invention belongs, and the like. Accordingly, definitions of these terms should be established based on the contents throughout the present specification. Throughout the specification, when a part "includes" a component, it means that the part may further include other components rather than excluding the other components unless otherwise specified.

All technical terms used in the present invention, unless otherwise defined, are used in the same meaning as those of ordinary skill in the art generally understand in the related field of the present invention. In addition, preferred methods or samples are described in the present specification, but those similar thereto or the equivalents thereof are included in the scope of the present invention. Contents of all publications described in the present specification by reference are incorporated into the present invention.

The inventors confirmed that the combined administration of cycloserine and lithium salt according to the present invention had a remarkably excellent effect of treating depression compared to each single administration, and completed the present invention.

In one aspect, the present invention provides a pharmaceutical composition for preventing or treating depression including: (i) cycloserine or a pharmaceutically acceptable salt thereof; and (ii) lithium or a pharmaceutically acceptable salt thereof.

In the pharmaceutical composition of the present invention, the cycloserine may be D-cycloserine represented by the following Formula 1:

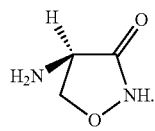

[Formula 1]

The lithium salt is one of the GSK-3 inhibitor series drugs. In addition to lithium as the GSK-3 inhibitor, examples of the GSK3 inhibitors may include inorganic atoms such as zinc and tungsten (including pharmaceutically acceptable salts thereof); ATP-competitive inhibitors such as indirubin, 6-BIO, hymenialdisine, dibromocantharelline, meridianin, aminopyrimidine, arylindolemaleimide, thiazole, paullone, and aloisine; non-ATP competitive inhibitors such as manzamine, furanosesquiterpene, thiadiazolidindione, halomethylketone, and L803-mts, and the like (see Eldar-Finkelman, Hagit, and Ana Martinez. "GSK-3 inhibitors: preclinical and clinical focus on CNS." Frontiers in molecular neuroscience 4 (2011): 32).

However, it is very difficult to predict even for those skilled in the art to which the present invention belongs, that when the lithium salt of the above-described GSK-3 inhibitors is administered in combination with cycloserine, an additive therapeutic effect is shown in the treatment of depression. However, the inventors performed a combination therapy of lithium, which is one of the GSK-3 inhibitors, or a pharmaceutically acceptable salt thereof, and cycloserine in a mouse model, and as a result, it was confirmed for the first time that the combination therapy was effective in the treatment of depression, which had a remarkably excellent effect compared to therapeutic effects of lithium salt or cycloserine, respectively (FIGS. 1 to 2).

In the present invention, the pharmaceutically acceptable salt refers to a salt commonly used in the pharmaceutical industry, and for example, may include salts of inorganic ions such as sodium, potassium, calcium, magnesium, lithium, copper, manganese, zinc, iron, and the like, salts of inorganic acids such as hydrochloric acid, phosphoric acid, sulfuric acid, and the like, and in addition thereto, may include salts of organic acids such as ascorbic acid, citric acid, tartaric acid, lactic acid, maleic acid, malonic acid, fumaric acid, glycolic acid, succinic acid, propionic acid, acetic acid, orotic acid, gluconic acid, acetylsalicylic acid, and the like, and amino acid salts such as lysine, arginine, guanidine, and the like. In addition, the pharmaceutically acceptable salt may include salts of organic ions such as tetramethyl ammonium, tetraethyl ammonium, tetrapropyl ammonium, tetrabutyl ammonium, benzyl trimethyl ammonium, benzethonium, and the like, that may be used in pharmaceutical reactions, purification and separation processes. However, types of salts meant in the present invention are not limited to salts that are listed above.

For example, preferred pharmaceutically acceptable salts of lithium may include, but are not limited to, lithium carbonate, lithium chloride, lithium acetate, lithium sulfate, lithium citrate, lithium orotate, and lithium gluconate.

Figure 2:
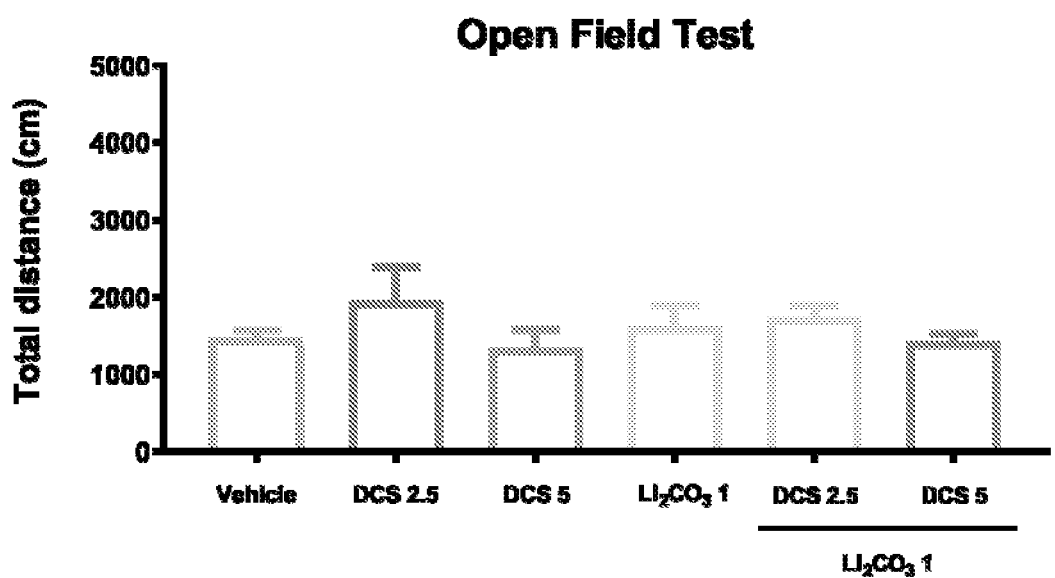
FIG. 2 is shows results of an open field test (OFT) in mouse depending on D-cycloserine, lithium salt, and the combination treatment thereof, respectively.

In an exemplary embodiment of the present invention, it was confirmed that the combined administration of cycloserine and lithium salt showed remarkably excellent results in behavioral tests such as a forced swimming test (FST), and the like, in experimental animals (FIGS. 1 to 2). Therefore, the pharmaceutical composition of the present invention may be effectively utilized for preventing or treating depression. The depression may be a single episode or recurrent major depressive disorder, or an anxiety disorder or depression with phobia, or manic depression such as type I bipolar disorder, type II bipolar disorder or circulatory disorder.

In the pharmaceutical composition of the present invention, a weight ratio of (i) the cycloserine or the pharmaceutically acceptable salt thereof; and (ii) the lithium or the pharmaceutically acceptable salt thereof may be 10:5 to 10:1, and specifically, about 2.5:1 or about 5:1. The pharmaceutical composition may include 10 to 50 mg of the cycloserine or the pharmaceutically acceptable salt thereof and 2.5 to 10 mg of the lithium or the pharmaceutically acceptable salt thereof, respectively. In one exemplary embodiment, the pharmaceutical composition may include 10 to 50 mg of D-cycloserine and 2.5 to 10 mg of lithium carbonate. Specifically, the pharmaceutical composition may include 12.5 to 25 mg of D-cycloserine per 5 mg of lithium carbonate. The inventors confirmed that when cycloserine and lithium salt were administered in combination in the above-described weight ratio, the combination therapy was particularly effective in treating depression (FIGS. 1 to 2).

The pharmaceutical composition of the present invention may be administered in a therapeutically effective amount. The therapeutically effective amount refers to a drug dosage that exerts a practical effect of preventing or treating depression. The suitable total daily dosage may be determined by the treating physician within proper medical judgment range. It is preferable to apply differently the specific therapeutically effective amount for a specific patient depending on various factors including the type and degree of the reaction to be achieved, the type and amount of drugs to be administered in combination, a specific composition used whether other preparations are used in some cases, the patient's age, weight, general health status, sex and diet, time of administration, route of administration, duration of treatment, and similar factors well known in the medical field.

The pharmaceutical composition of the present invention may be administered in divided doses once to several times a day. For example, cycloserine or the pharmaceutically acceptable salt thereof and lithium or the pharmaceutically acceptable salt thereof may be administered based on a mouse at a dose of 0.2 to 50 mg/kg and 0.1 to 100 mg/kg, respectively, and specifically 2 to 7.5 mg/kg of cycloserine or the pharmaceutically acceptable salt thereof per 1 mg/kg of lithium or the pharmaceutically acceptable salt thereof may be administered.

It was confirmed in Examples of the present invention that as a result of administering cycloserine and the lithium salt to experimental animals (for example, mice) in various dosage ranges, forced swimming test (FST) results were significantly improved in a group that was administered with about 2.5 mg/kg, or 5 mg/kg of D-cycloserine and about 1 mg/kg of lithium carbonate in combination (FIG. 1).

Therefore, it is possible to convert the preferred dose in human in consideration of the optimal dose to be administered to mouse confirmed in the present invention, the mouse-human dose-response relationship, and no-observed-adverse-effect level (NOAEL), and the like. The dose conversion factor may be expressed by using the human equivalent dose (HED) calculation method described in the document (see, FDA, US. "Guidance for Industry, Estimating the maximum safe starting dose in initial clinical trials for therapeutics in adult healthy volunteers." FDA, ed (2005)). The mouse-human dose conversion factor suggested in the above document is 12.3, and a dose of A/12.3 (mg/kg) is derived by dividing a dose (A) of the drug identified in the mouse by the conversion factor. In general, one tablet is made for an adult weighing 60 kg. If the value of A/12.3 (mg/kg) is multiplied by 60 kg, the dose of about 5×A (mg), which is the human dose, is derived. Therefore, with reference to the optimal mouse dose ratio of D-cycloserine and lithium carbonate identified in the examples of the present invention, it is possible to derive a preferred drug dose to be administered to humans.

Accordingly, doses of D-cycloserine and lithium carbonate included in the pharmaceutical composition of the present invention are preferably 10 to 50 mg and 2.5 to 10 mg, respectively, and more preferably 12.5 to 25 mg of D-cycloserine per 5 mg of lithium carbonate is administered. The inventors also confirmed that the effect of treating depression is maximized in the above-described range compared to a case where a dose group of D-cycloserine and lithium carbonate is higher than the above-described range. This is the first confirmation that the effect of treating depression is improved when administering D-cycloserine and lithium carbonate in combination at a dose much lower than a dose used in the single preparation of D-cycloserine or lithium carbonate.

The pharmaceutical composition of the present invention may be administered orally or parenterally, and is preferably administered orally. In addition, the pharmaceutical composition of the present invention may be used in combination with one or more central nervous system drugs. For example, the pharmaceutical composition may be used in combination with additional pharmaceutical antidepressants, herbal antidepressants, anticonvulsants, mood stabilizers, antipsychotics, benzodiazepines, or a combination thereof for effective treatment of depression.

The pharmaceutical composition of the present invention may include a pharmaceutically acceptable carrier, excipient, and/or diluent for administration. Examples of the carrier, excipient and/or diluent may include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils.

The pharmaceutical composition of the present invention may be prepared in a pharmaceutical formulation using a method well known in the art. In the preparation of the formulation, the active ingredient may be mixed or diluted with a carrier, or encapsulated in a carrier in the form of a container. When the pharmaceutical composition of the present invention is prepared in a formulation for oral administration, for example, the pharmaceutical composition may be formulated as tablets, troches, lozenges, water-soluble or oily suspensions, powders or granules, emulsions, hard or soft capsules, syrups or elixirs.

In one aspect, the present invention provides a method for preventing or treating depression including: administering to a patient a therapeutically effective amount of (i) cycloserine or a pharmaceutically acceptable salt thereof; and (ii) lithium or a pharmaceutically acceptable salt thereof. In another aspect, the present invention provides a use of (i) cycloserine or a pharmaceutically acceptable salt thereof; and (ii) lithium or a pharmaceutically acceptable salt thereof in preparation of a medicament for preventing or treating depression. The cycloserine, lithium, salt, and the like are the same as described above.

In one aspect, the present invention provides a combination for preventing or treating depression including: (i) a first preparation including cycloserine or a pharmaceutically acceptable salt thereof; and (ii) a second preparation including lithium or a pharmaceutically acceptable salt thereof.

In the present invention, the term "combination" refers to a combination of two or more active substances in a formulation and a combination in the sense of individual formulations of active substances that are administered at specified intervals from each other in treatment. Thus, the term "combination", when described in connection with the present invention, includes the clinical realization of co-administration of two or more therapeutically effective compounds.

In the combination of the present invention, the cycloserine may be D-cycloserine, and lithium carbonate may be specifically selected as the pharmaceutically acceptable salt of lithium.

In the combination of the present invention, doses of the cycloserine or the pharmaceutically acceptable salt thereof in the first preparation and the lithium or the pharmaceutically acceptable salt thereof in the second preparation may be 10 to 50 mg and 2.5 to 10 mg, respectively, and more preferably 12.5 to 25 mg of D-cycloserine per 5 mg of lithium carbonate is administered. In the combination of the present invention, the first preparation and/or the second preparation may be administered parenterally or orally, respectively, and preferably may be administered orally.

In the combination of the present invention, the first preparation and the second preparation may be administered simultaneously or at different times.

The combination of the present invention may be a combination preparation including the first preparation and the second preparation, and specifically may be a combination preparation administered orally.

In the combination of the present invention, a weight ratio of the cycloserine or the pharmaceutically acceptable salt thereof included in the first preparation; and the lithium or the pharmaceutically acceptable salt thereof included in the second preparation may be 10:5 to 10:1, and specifically, about 2.5:1 or about 5:1. In this case, doses of the cycloserine or the pharmaceutically acceptable salt thereof included in the first preparation and the lithium or the pharmaceutically acceptable salt thereof included in the second preparation may be 10 to 50 mg and 2.5 to 10 mg, respectively, and more preferably 12.5 to 25 mg of D-cycloserine per 5 mg of lithium carbonate is administered.

In one aspect, the present invention provides an adjuvant pharmaceutical composition of lithium for preventing or treating depression including cycloserine or a pharmaceutically acceptable salt thereof.

In the present invention, the term "adjuvant" refers to a use in which even though preventive or therapeutic effects of the drug alone administered as an auxiliary are relatively low, an effect of preventing or treating depression is remarkably improved when administered in combination with other central nervous system drugs.

In the composition, the cycloserine may be D-cycloserine, and lithium carbonate may be specifically selected as the pharmaceutically acceptable salt of lithium.

In the adjuvant pharmaceutical composition of lithium for preventing or treating depression, the weight of the cycloserine or the pharmaceutically acceptable salt thereof may be 2 to 10 times, or 2.25 to 7.5 times, and specifically about 2.5 times, 5 times, or 7.5 times the weight of the lithium or the pharmaceutically acceptable salt thereof used for preventing or treating depression. In this case, the cycloserine or the pharmaceutically acceptable salt thereof included in the adjuvant pharmaceutical composition of lithium for preventing or treating depression may have the weight of about 10 to 50 mg, which may reduce the weight of the lithium or the pharmaceutically acceptable salt thereof used for preventing or treating depression up to about 2.5 to 10 mg.

The composition of the present invention may be a pharmaceutical composition or a food composition. When the composition is used as the food composition, cycloserine and lithium or a pharmaceutically acceptable salt thereof may be added as it is or may be used together with other foods or food ingredients, and may be appropriately used according to a conventional method. The composition may include food supplementary additives acceptable for food in addition to an active ingredient, and an amount of the active ingredient mixed may be appropriately determined according to the purpose of use (prevention, health or therapeutic treatment).

The food composition of the present invention may include a health functional food. The term "health functional food" used in the present invention refers to food manufactured and processed in the form of tablets, capsules, powders, granules, liquids pills, and the like, using raw materials or ingredients that have useful functionality for the human body. Here, the term "functionality" refers to obtaining useful effects for health use such as controlling nutrients, physiological action, or the like, on the structure and function of the human body.

In addition, there is no limitation on the type of health food that the composition of the present invention can be used. Further, the composition including cycloserine and/or lithium as an active ingredient of the present invention may be prepared by mixing other suitable adjuvant ingredients and known additives that may be contained in health functional foods depending on the selection of those skilled in the art. Examples of the food that can be added may include meat, sausage, bread, chocolate, candy, snacks, confectionery, pizza, ramen, other noodles, gum, dairy products including ice cream, various soups, beverages, tea, drinks, alcoholic beverages, vitamin complexes, and the like, and the food may be prepared by adding an extract according to the present invention as a main component into squeezed juice, tea, jelly, juice, and the like.

All the matters described in compositions, treatment methods and uses of the present invention are applied equally as long as they are inconsistent with each other.

The present invention will be described in more detail through the following Examples. However, these Examples are provided only to embody the contents of the present invention and the present invention is not limited thereto.

Example 1 Forced Swimming Test (FST) Results Depending on Combined Administration of Cycloserine and Lithium In order to test an effect of reducing depression depending on administration of the pharmaceutical composition of the present invention, mice were subjected to a forced swimming test (FST). The FST, which is to measure a coping strategy for acute stress that inevitably occurs, is an animal behavioral experiment commonly used to measure antidepressant effects.

To confirm the effect of reducing depression by combined administration of D-cycloserine (DCS) and lithium, 10 ml/kg of the preparation was administered to all groups of mice (C57BL6). Each group of mice was administered with the vehicle (DW, control group, n=22), DCS 2.5 (DCS 2.5 mg/kg single treatment group, n=6), DCS 5 (DCS 5 mg/kg single treatment group, n=6), $Li_2CO_3$ 1 ($Li_2CO_3$ 1 mg/kg single treatment group, n=6), DCS 1+Li$_2$CO$_3$ 1 (DCS 1 mg/kg and Li$_2$CO$_3$ 1 mg/kg combination treatment group, n=13), DCS 2.5+Li$_2$CO$_3$ 1 (DCS 2.5 mg/kg and Li$_2$CO$_3$ 1 mg/kg combination treatment group, n=14), DCS 5+Li$_2$CO$_3$ 1 (DCS 5 mg/kg and Li$_2$CO$_3$ 1 mg/kg combination treatment group, n=14), DCS 10+Li$_2$CO$_3$ 1 (DCS 10 mg/kg and Li$_2$CO$_3$ 1 mg/kg combination treatment group, n=14). After 1 hour, the forced swimming test (FST) that measures depression-like behavior was performed on the mice.

Specifically, each group of mice was individually placed in a 3 L Pyrex beaker (13 cm in diameter, 24 cm in height), and the beakers were filled with 27.5±1.5° C. of water up to a depth of 9 cm. All mice were forced to swim for 6 minutes, and immobility time was measured for the last 4 minutes of the experiment. The immobility time is defined as the RNR time taken while the mouse is floating without struggling or taking only the movement required for keeping the mouse's head above the water surface.

As a result, each group administered with DCS or Li$_2$CO$_3$ alone did not show statistical significance as compared to the control group administered with the vehicle, but a group that was subjected to FST in an hour after being administered with DCS and LiCl in combination, showed a significant decrease in immobility (FIGS. 1 and 2). In addition, it was shown that the immobility was significantly decreased even a week after DCS and Li$_2$CO$_3$ were administered in combination (FIG. 1).

In addition, as a result of the open field test, it was confirmed that it did not affect the activity of the animal such as a distance that the mouse moved for a predetermined period of time (15 minutes) in the experiment (FIG. 2). This confirmation proved that the decrease in immobility time of the group administered in combination at the specific ratio, which was confirmed in the results of the FST experiment, was not caused by the increase in activity of the corresponding groups.

The above results showed that the combined administration of cycloserine and lithium can be effectively utilized as a combined therapeutics for preventing or treating depression effects as an antidepressant.

The invention claimed is:

1. A method for preventing or treating depression comprising administering to a subject in need there of a therapeutically effective amount of (i) cycloserine or a pharmaceutically acceptable salt thereof; and (ii) lithium or a pharmaceutically acceptable salt thereof,
wherein a weight ratio of (i) the cycloserine or the pharmaceutically acceptable salt thereof; and (ii) the lithium or the pharmaceutically acceptable salt thereof is 10:5 to 10:1.

2. The method of claim 1, wherein the cycloserine is D-cycloserine represented by Formula 1:

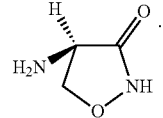

[Formula 1]

3. The method of claim 1, wherein the pharmaceutically acceptable salt of lithium is lithium carbonate.

4. The method of claim 1, wherein (i) 10 to 50 mg of the cycloserine or the pharmaceutically acceptable salt thereof; and (ii) 2.5 to 10 mg of the lithium or the pharmaceutically acceptable salt thereof are administered to the subject.

5. The method of claim 4, wherein 12.5 to 25 mg of D-cycloserine per 5 mg of lithium carbonate is administered to the subject.

6. The method of claim 1, wherein the pharmaceutical composition is administered orally.

* * * * *